United States Patent

Dunn et al.

[11] Patent Number: 6,066,735
[45] Date of Patent: May 23, 2000

[54] PROCESS FOR PREPARING SILDENAFIL

[75] Inventors: Peter James Dunn; Albert Shaw Wood, both of Sandwich, United Kingdom

[73] Assignee: Pfizer Inc., New York, N.Y.

[21] Appl. No.: 09/360,128

[22] Filed: Jul. 23, 1999

Related U.S. Application Data

[62] Division of application No. 08/869,532, Jun. 6, 1997, Pat. No. 5,955,611.

[30] Foreign Application Priority Data

Jun. 14, 1996 [GB] United Kingdom ............ 9612514

[51] Int. Cl.⁷ .................. C07D 403/12; C07D 295/26
[52] U.S. Cl. ............................ 544/371; 544/383
[58] Field of Search ..................... 544/371, 383

[56] References Cited

U.S. PATENT DOCUMENTS 4,871,843  10/1989  Roger et al. ........................ 540/575

FOREIGN PATENT DOCUMENTS

| 0463756 | 1/1992 | European Pat. Off. . |
| 0526004 | 2/1992 | European Pat. Off. . |
| 9428902 | 12/1994 | WIPO . |
| 98/49166 | 11/1998 | WIPO . |
| 99/64004 | 12/1999 | WIPO . |

OTHER PUBLICATIONS

Harriet W. Hamilton, et al. J. Med. Chem. 1987, 30, 91–96.

*Primary Examiner*—Emily Bernhardt
*Attorney, Agent, or Firm*—Peter C. Richardson; Gregg C. Benson; James T. Jones

[57] ABSTRACT

A process for the preparation of a compound of formula (I):

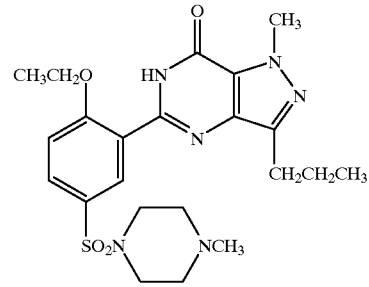

which comprises cyclization of a compound of formula (II):

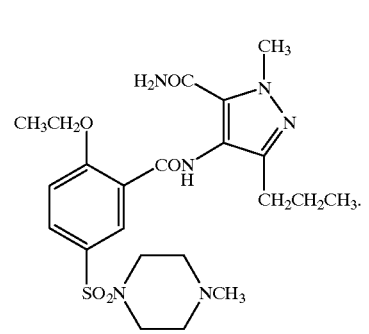

2 Claims, No Drawings

PROCESS FOR PREPARING SILDENAFIL

This is a division of application Ser. No. 09/869,532, filed on Jun. 6, 1997, now U.S. Pat. No. 5,955,611, entitled "Process For Preparing Sildenafil".

The invention relates to a process for the preparation of the compound of formula (I):

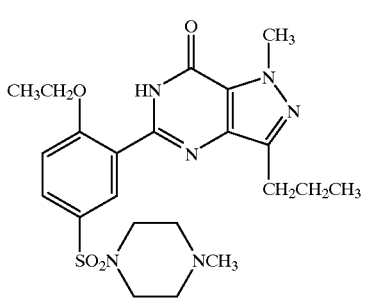

known as 5-[2-ethoxy-5-(4-methylpiperazin-1-ylsulphonyl) phenyl]-1-methyl-3-n-propyl-1,6-dihydro-7H-pyrazolo[4,3-d]pyrimidin-7-one or sildenafil, and also to intermediates used therein. Sildenafil, which was originally disclosed in EP-A-0463756, has been found to be particularly useful in the treatment of, inter alia, male erectile dysfunction: see WO-A-94/28902.

More specifically, the invention concerns a process for the preparation of sildenafil which is more efficient than that disclosed in EP-A-0463756 and which, surprisingly, can provide directly sildenafil of clinical quality standard, thus obviating the need for subsequent purification steps. In this context, sildenafil of clinical quality standard means material of sufficient purity for administration to humans.

The key step in the over-all process involves the ring-closure of the immediate precursor to sildenafil, i.e. the bis-amide of formula (II):

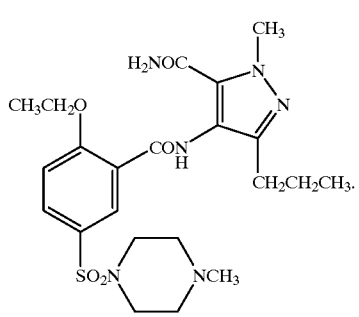

Thus the invention provides a process for the preparation of a compound of formula (I) which comprises cyclisation of a compound of formula (II).

In a preferred embodiment, the cyclisation is carried out in the presence of a base, preferably in a solvent, optionally in the presence of hydrogen peroxide or a peroxide salt, and is followed, where necessary, by neutralisation of the reaction mixture.

A suitable base may be selected from the group consisting of a metal salt of a $C_1$–$C_{12}$ alkanol, a $C_3$–$C_{12}$ cycloalkanol, a ($C_3$–$C_8$ cycloalkyl)$C_1$–$C_6$ alkanol, ammonia, a $C_1$–$C_{12}$ alkylamine, a di($C_1$–$C_{12}$ alkyl)amine, a $C_3$–$C_8$ cycloalkylamine, a N-($C_3$–$C_8$ cycloalkyl)-N-($C_1$–$C_{12}$ alkyl) amine, di($C_3$–$C_8$ cycloalkyl)amine, a ($C_3$–$C_8$ cycloalkyl) $C_1$–$C_6$ alkylamine, a N-($C_3$–$C_8$ cycloalkyl)$C_1$–$C_6$-alkyl-N-($C_1$–$C_{12}$ alkyl)amine, a N-($C_3$–$C_8$ cycloalkyl)$C_1$–$C_6$ alkyl-N-($C_3$–$C_8$ cycloalkyl)amine, a di[($C_3$–$C_8$ cycloalkyl)$C_1$–$C_6$ alkyl]amine and a heterocyclic amine selected from the group consisting of imidazole, triazole, pyrrolidine, piperidine, heptamethyleneimine, morpholine, thiomorpholine and a 1-($C_1$–$C_4$ alkyl)piperazine; a metal hydride, fluoride, hydroxide, oxide, carbonate and bicarbonate; wherein the metal is selected from the group consisting of lithium, sodium, potassium, rubidium, cesium, beryllium, magnesium, calcium, strontium, barium, aluminium, indium, thallium, titanium, zirconium, cobalt, copper, silver, zinc, cadmium, mercury and cerium; and a $C_7$–$C_{12}$ bicyclic amidine.

Preferably the base is selected from the group consisting of an alkali or alkaline earth metal salt of a $C_1$–$C_{12}$ alkanol, a $C_3$–$C_{12}$ cycloalkanol and a ($C_3$–$C_8$ cycloalkyl) $C_1$–$C_6$ alkanol; an alkali metal salt of ammonia, a N-(secondary or tertiary $C_3$–$C_6$ alkyl)-N-(primary, secondary or tertiary $C_3$–$C_6$ alkyl)amine, a $C_3$–$C_8$ cycloalkylamine, a N-($C_3$–$C_8$ cycloalkyl)-N-(primary, secondary or tertiary $C_3$–$C_6$ alkyl) amine, a di($C_3$–$C_8$ cycloalkyl)amine and 1-methylpiperazine; and an alkali or alkaline earth metal hydride, hydroxide, oxide, carbonate and bicarbonate; 1,5-diazabicyclo[4.3.0]non-5-ene and 1,8-diazabicyclo[5.4.0]undec-7-ene.

A suitable solvent may be selected from the group consisting of a $C_1$–$C_{12}$ alkanol, a $C_3$–$C_{12}$ cycloalkanol, a ($C_3$–$C_8$ cycloalkyl)$C_1$–$C_6$ alkanol, a $C_3$–$C_9$ alkanone, a $C_4$–$C_{10}$ cycloalkanone, a $C_5$–$C_{12}$ alkyl ether, 1,2-dimethoxyethane, 1,2-diethoxyethane, diglyme, tetrahydrofuran, 1,4-dioxan, benzene, toluene, xylene, chlorobenzene, dichlorobenzene, acetonitrile, dimethyl sulphoxide, sulpholane, dimethylformamide, dimethylacetamide, N-methylpyrrolidin-2-one, pyrrolidin-2-one, pyridine and water, and mixtures thereof.

Preferably the solvent is selected from the group consisting of ethanol, 2-propanol, a secondary or tertiary $C_4$–$C_{12}$ alkanol, a $C_3$–$C_{12}$ cycloalkanol, a tertiary $C_4$–$C_{12}$ cycloalkanol, a secondary or tertiary ($C_3$–$C_7$ cycloalkyl) $C_2$–$C_6$ alkanol, a $C_3$–$C_9$ alkanone, 1,2-dimethoxyethane, 1,2-diethoxyethane, diglyme, tetrahydrofuran, 1,4-dioxan, toluene, xylene, chlorobenzene, 1,2-dichlorobenzene, acetonitrile, dimethyl sulphoxide, sulpholane, dimethylformamide, N-methylpyrrolidin-2-one, pyrdine and water, and mixtures thereof.

Further preferred features are that the quantity of base employed is from 1.0 to 5.0 molecular equivalents and that the reaction is carried out at from 50 to 170° C. for from 3 to 170 hours.

In a more preferred process the base is selected from the group consisting of the lithium, sodium and potassium salts of a $C_1$–$C_{12}$ alkanol, a $C_4$–$C_{12}$ cycloalkanol, ammonia, cyclohexylamine and 1-methylpiperazine; the hydride salts of lithium, sodium and potassium; cesium carbonate; and barium oxide; the solvent is selected from the group consisting of ethanol, a tertiary $C_4$–$C_{10}$ alcohol, a tertiary $C_5$–$C_8$ cycloalkanol, tetrahydrofuran, 1,4-dioxan and acetonitrile, the reaction is carried out at from 60 to 105° C. and the quantity of base employed is from 1.1 to 2.0 molecular equivalents:

Even more preferred is a process wherein the base is selected from the group consisting of the $C_1$–$C_{12}$ alkoxide and hydride salts of lithium, sodium and potassium, sodamide, sodium cyclohexylamide and cesium carbonate; the solvent is selected from the group consisting of ethanol, t-butanol, t-amyl alcohol, 1-methylcyclohexanol, tetrahydrofuran and 1,4-dioxan; and the reaction is conducted for from 3 to 60 hours.

A particularly preferred process is that wherein the base is selected from the group consisting of sodium ethoxide, sodium t-butoxide, potassium t-butoxide and sodium hydride; and the solvent is selected from the group consisting of ethanol, t-butanol, t-amyl alcohol and tetrahydrofuran.

In the above definitions, unless otherwise stated, an alkyl chain or cycloalkyl ring may branched or unbranched.

The compound of formula (I) may be isolated and purified by conventional techniques. For example, when (I) is produced in the form of a salt, by neutralisation of the optionally prediluted reaction mixture, followed by collection of the product by filtration/extraction and optional crystallisation thereof.

Alternatively, the compound of formula (I) may be conveniently isolated and/or purified by standard chromatographic procedures.

The compound of formula (II) required for the preparation of the compound of formula (I) may be obtained by the route depicted in the following reaction scheme using conventional procedures.

Thus the compound of formula (IV) may be prepared by chlorosulphonylation of 2-ethoxybenzoic acid, i.e. the compound of formula (III). Typically, (III) is added to an ice-cooled mixture of about 1 mol. equiv. of thionyl chloride and about 4 mol. equivs. of chlorosulphonic acid, whilst maintaining the reaction temperature below 25° C.; the reaction is then allowed to continue at room temperature until complete.

Conversion of (IV) to the compound of formula (V) is achieved by N-sulphonylation of 1-methylpiperazine and may be conducted in a one-step or two-step procedure. In a one-step procedure, about 2.3 mol. equivs. of 1-methylpiperazine are added to an aqueous suspension of (IV) at about 10° C., whilst maintaining the reaction temperature below 20° C.; the temperature of the resulting reaction mixture is then held at about 10° C. Alternatively, the quantity of 1-methylpiperazine can be reduced to about 1.1 mol. equiv. by employing about 1 mol. equiv. of sodium hydroxide as auxiliary base. In a two-step procedure, a

SCHEME

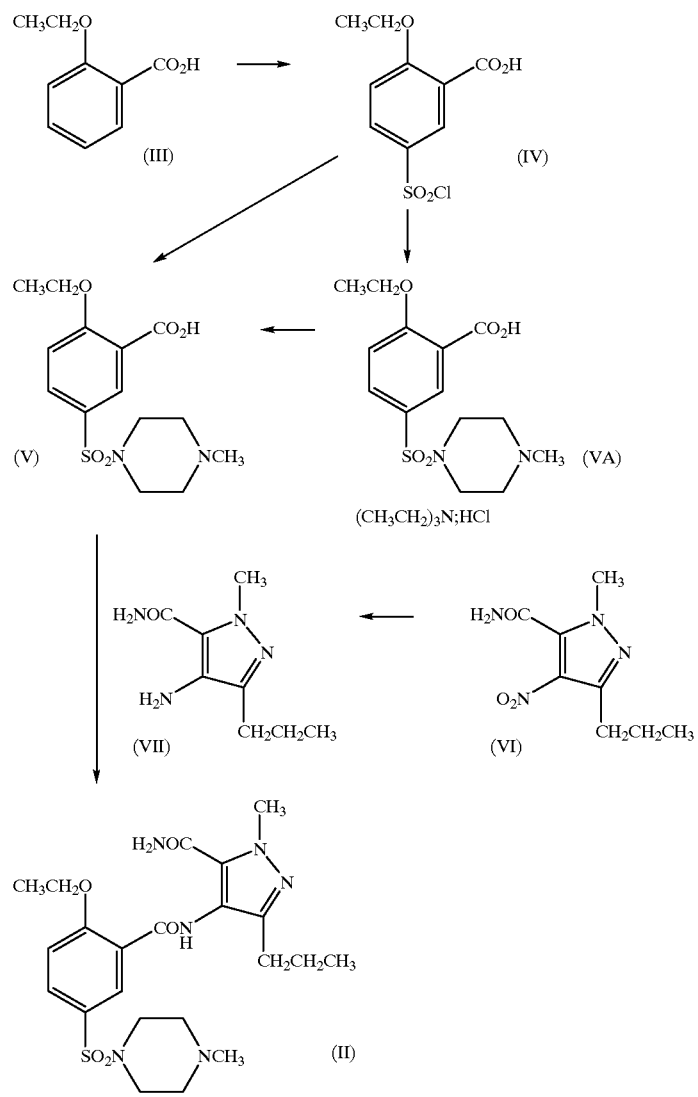

solution of (IV) in a suitable solvent, e.g. acetone, is added to a mixture of about a 10% excess of 1-methylpiperazine and about a 10% excess of a suitable acid acceptor, e.g. a tertiary base such as triethylamine, whilst maintaining the reaction temperature below 20° C. When triethylamine is employed as auxiliary base, an intermediate hydrochloride-triethylamine double salt of (V), identified as the compound of formula (VA), is isolated. This salt may be transformed to (V) by treatment with water.

A convenient alternative route to (V) is to employ a $C_1$–$C_4$ alkyl 2-ethoxybenzoate (obtained by conventional esterification of (III)) as the chlorosulphonylation substrate, followed by treatment of the resulting sulphonyl chloride with 1-methylpiperazine as described above, then subsequent standard hydrolysis of the ester group. Other synthetic options for obtaining (V) from salicylic acid and its derivatives will be apparent to the person skilled in the art.

Coupling of (V) with the compound of formula (VII) may be achieved by any of the plethora of amide bond-forming reactions well known to those skilled in the art. For example, the carboxylic acid function of (V) is first of all activated using about a 5% excess of a reagent such as N,N'-carbonyldiimidazole in a suitable solvent, e.g. ethyl acetate, at from about room temperature to about 80° C., followed by reaction of the intermediate imidazolide with (VII) at from about 20 to about 60° C.

The aminopyrazole (VII) is obtainable by conventional reduction of the corresponding nitropyrazole (VI), e.g. using palladium-catalysed hydrogenation in a suitable solvent such as ethyl acetate. The resulting solution of (VII) may be used directly, after filtration, in the coupling reaction with (V).

The cyclisation reaction of (II) to provide the compound of formula (I) has been achieved in yields of up to 95%. Thus the over-all yield of (I) based on the benzoic acid derivative (III) as starting material, depending on whether the one-step or two-step sulphonylation procedure is used, can be as high as 51.7% or 47.8% respectively. This compares very favourably with the process disclosed in EP-A-0463756 in which the over-all yield of (I) from 2-ethoxybenzoyl chloride (and thus from (III) also, assuming that the acid chloride derivative can be generated quantitatively therefrom) is 27.6%. In an alternative comparison, the over-all yield of (I) based on the nitropyrazole (VI) can be as high as 85.2% in the presently disclosed process whilst, in the process disclosed in EP-A-0463756, the over-all yield of (I) from (VI) is 23.1%.

Clearly then, the alternative process to (I) disclosed hereinbefore can be considerably more efficient and advantageous than that previously disclosed, and the intermediates of formulae (II), (V) and (VA) also form part of the invention.

Alternatively, the cyclisation of a compound of formula (II) to a compound of formula (I) may be conducted under neutral or acidic conditions.

Under neutral conditions, the compound of formula (II) is heated, optionally in the presence of a solvent and/or optionally in the presence of a dehydrating agent and/or mechanical water-removal system, e.g. a Dean-Stark apparatus.

A suitable solvent may be selected from the group consisting cf 1,2-dichlorobenzene, dimethyl sulphoxide, sulpholane, N-methylpyrrolidin-2-one and pyrrolidin-2-one, and mixtures thereof.

Preferably the solvent is 1,2-dichlorobenzene, sulpholane or N-methylpyrrolidin-2-one.

A suitable dehydrating agent may be selected from the group consisting of anhydrous potassium carbonate, anhydrous sodium carbonate, anhydrous magnesium sulphate, anhydrous sodium sulphate, phosphorus pentoxide and molecular sieves.

Preferably, the dehydrating agent is molecular sieves.

Preferably also, the reaction is carried out at from 180 to 220° C. for from 0.5 to 72 hours.

Under acidic conditions, the cyclisation is carried out by reaction of a compound of formula (II) with a protic acid or Lewis acid, optionally in the presence of a solvent.

A suitable protic acid may be selected from the group consisting of an inorganic acid, an organo-sulphonic acid, an organo-phosphonic acid and an organo-carboxylic acid.

Preferably the protic acid is concentrated sulphuric acid, phosphoric acid or p-toluenesulphonic acid.

A suitable Lewis acid may be selected from the group consisting of boron trifluoride, boron trichloride, boron tribromide, aluminium chloride, aluminium bromide, silicon tetrachloride, silicon tetrabromide, stannic chloride, stannic bromide, phosphorus pentachloride, phosphorus pentabromide, titanium tetrafluoride, titanium tetrachloride, titanium tetrabromide, ferric chloride, zinc fluoride, zinc chloride, zinc bromide, zinc iodide, mercuric chloride, mercuric bromide and mercuric iodide.

Preferably the Lewis acid is boron trifluoride, aluminium chloride, silicon tetrachloride, stannic chloride, titanium tetrachloride, ferric chloride or zinc chloride.

A suitable solvent may be selected from the group consisting of a $C_5$–$C_{12}$ alkane, a $C_5$–$C_8$ cycloalkane, a $C_1$–$C_{12}$ alkanoic acid, a $C_1$–$C_4$ alkanol, a $C_3$–$C_9$ alkanone, a $C_5$–$C_{12}$ alkyl ether, 1,2-dimethoxyethane, 1,2-diethoxyethane, diglyme, tetrahydrofuran, 1,4-dioxan, benzene, toluene, xylene, chlorobenzene, dichlorobenzene, nitrobenzene, dichloromethane, dibromomethane, 1,2-dichloroethane, acetonitrile, dimethyl sulphoxide, sulpholane, dimethylformamide, dimethylacetamide, N-methylpyrrolidin-2-one and pyrrolidin-2-one, and mixtures thereof.

Preferably the solvent is glacial acetic acid, tetrahydrofuran, 1,4-dioxan or chlorobenzene.

Preferably also, the reaction is carried out at from 65 to 210° C. for from 6 to 300 hours.

The syntheses of the compound of formula (I) and the intermediates thereto are described in the following Examples and Preparations. In cases where the compound of formula (I) was not isolated and (if necessary) purified, the yields thereof were determined, and reaction mixtures analysed, by quantitative thin layer chromatography (TLC), using Merck silica gel 60 plates and toluene:methylated spirit:0880 aqueous ammonia mixtures as solvent systems, and/or high performance liquid chromatography (HPLC), using Gilson equipment with a 15 cm reverse phase C18 column and triethylamine:phosphoric acid buffer in aqueous acetonitrle:methanol mixtures as mobile phases.

$^1$H Nuclear magnetic resonance (NMR) spectra were recorded using a Varian Unity 300 spectrometer and were in all cases consistent with the proposed structures. Characteristic chemical shifts ($\delta$) are given in parts-per-million downfield from tetramethylsilane using conventional abbreviations for designation of significant peaks: e.g. s, singlet; d, doublet; t, triplet; q, quartet; h, hextet; m, multiplet; br, broad.

Room temperature means 20–25° C.

TITLE COMPOUND

5-[2-Ethoxy-5-(4-methylpiperazin-1-ylsulphonyl)phenyl]-1-methyl-3-n-propyl-1,6-dihydro-7H-pyrazolo[4,3-d]pyrimidin-7-one

EXAMPLE 1

Potassium t-butoxide (3.37 g, 0.030 mol) was added to a stirred suspension of the title compound of Preparation 4

(12.32 g, 0.025 mol) in t-butanol (61 ml) and the resulting mixture heated under reflux for 8 hours, then allowed to cool to room temperature. Water (62.5 ml) was added and then the resulting solution filtered into a speck-free flask and treated dropwise with a speck-free solution of concentrated hydrochloric acid (2.3 ml) in water (62.5 ml). The precipitated product was granulated at pH 7 and 10° C. for 1 hour, collected by filtration, washed with water and dried under vacuum to give the title compound (10.70 g, 90.2%) m.p. 189–190° C. Found: C,55.55; H,6.34; N,17.69. $C_{22}H_{30}N_6O_4S$ requires C,55.68; H,6.37; N,17.71%. δ ($CD_3SOCD_3$): 0.94(3H,t), 1.32(3H,t), 1.73(2H,h), 2.15(3H,s), 2.35(4H,br s), 2.76(2H,t), 2.88(4H,br s), 4.14(3H,s), 4.18(2H,q), 7.36(1H,d), 7.80(2H,m), 12.16(1H,br s).

Analysis of the product by HPLC and quantitative TLC indicated that clinical quality material had been obtained directly from the reaction.

The yield of clinical quality material can be increased to 95% by conducting the cyclisation under more concentrated conditions.

EXAMPLES 2–5

Clinical quality material was obtained by variation of the solvent, using procedures similar to that described in Example 1, as summarised in Table 1. As for Example 1, the reactions were carried out at reflux temperature, except in the cases of Examples 2 and 5 where a temperature of 10° C. was employed.

TABLE 1

| EXAMPLE | SOLVENT | REACTION TIME (HOURS) | % YIELD |
| --- | --- | --- | --- |
| 2 | t-amyl alcohol | 5 | 78 |
| 3 | ethanol | 9.5 | 83 |
| 4 | tetrahydrofuran | 32 | 81 |
| 5 | 1-methylcyclohexanol | 4 | 65 |

EXAMPLES 6–9

Clinical quality material was obtained by variation of the solvent and the base, using procedures similar to that described in Example 1, as summarised in Table 2. The reactions were carried out at reflux temperature, except in the case of Example 9 where a temperature of 100° C. was employed.

TABLE 2

| EXAMPLE | BASE | SOLVENT | REACTION TIME (HOURS) | % YIELD |
| --- | --- | --- | --- | --- |
| 6 | sodium ethoxide | t-butanol | 10 | 86 |
| 7 | sodium ethoxide | ethanol | 7 | 82.5 |
| 8 | sodium hydride | tetrahydrofuran | 48 | 84 |
| 9 | cesium carbonate | t-amyl alcohol | 17 | 71 |

EXAMPLE 10

Clinical quality material (88%) was obtained by variation of the cation, using a procedure similar to that described in Example 1. when sodium t-butoxide was used as base and the reaction was conducted for 24 hours.

EXAMPLE 11

Clinical quality material (71%) was obtained by variation of the molar ratio of base, using a procedure similar to that described in Example 1, when potassium t-butoxide (5.0 mol.equiv.) was used and the reaction was conducted at reflux temperature for 18 hours.

EXAMPLE 12

Further variation of the reaction conditions of Example 1, using 1.6 mol. equiv. of potassium t-butoxide (4.49 g, 0.040 mol) at 60° C. for 55 hours, provided the title compound (87%) of purity >99% by HPLC and TLC analyses.

EXAMPLE 13

Title compound (87%) of purity >99% by HPLC and TLC analyses was obtained, using a procedure similar to that described in Example 1, when 1,4-dioxan was used as solvent and the reaction was conducted at 100° C. for 4 hours.

EXAMPLE 14

Title compound (85%) of purity >99% by HPLC and TLC analyses was obtained, using a procedure similar to that described in Example 1, when 1,2-dimethoxyethane was used as solvent and the reaction was conducted for 30 hours.

EXAMPLE 15

Title compound (83%) of purity >99% by HPLC and TLC analyses was obtained, using a procedure similar to that described in Example 1, when 3,7-dimethyloctan-3-ol was used as solvent and the reaction was conducted at 100° C. for 16 hours.

EXAMPLE 16

Title compound (74%) of purity >99% by HPLC and TLC analyses was obtained, using a procedure similar to that described in Example 1, when sodium n-decoxide was used as base, 1,4-dioxan was used as solvent and the reaction was conducted at 100° C. for 20 hours.

EXAMPLE 17

Title compound (85%) of purity >99% by HPLC and TLC analyses was obtained, using a procedure similar to that described in Example 1, when sodamide was used as base, 1,4-dioxan was used as solvent and the reaction was conducted at 100° C. for 18 hours.

EXAMPLE 18

Title compound (91%) of purity >99% by HPLC and TLC analyses was obtained, using a procedure similar to that described in Example 1, when sodium cyclohexylamide was used as base 1,4-dioxan was used as solvent and the reaction was conducted at 100° C. for 6.5 hours.

EXAMPLE 19

Title compound (84%) of purity >99% by HPLC and TLC analyses was obtained, using a procedure similar to that described in Example 1, when sodium 4-methylpiperatide was used as base, 1,4-dioxan was used as solvent and the reaction was conducted at 100° C. for 8 hours.

EXAMPLES 20–21

Under reaction conditions similar to those described in Example 1, the use of sodium methoxide in methanol for 32 hours furnished a four-component mixture from which the title compound was isolated in a chromatographed yield of 34.5%, whilst the use of potassium t-butoxide in methanol for 40 hours afforded a product mixture which, by TLC and NMR spectroscopic analyses, contained an estimated yield of 69% of the title compound.

EXAMPLE 22

Under reaction conditions similar to those described in Example 1, the use of potassium t-butoxide in anhydrous dimethyl sulphoxide at 100° C. for 50 hours afforded a crude product (88% wt. yield) which, by TLC and HPLC analyses, contained an estimated yield of 24% of the title compound.

EXAMPLE 23

Under reaction conditions similar to those described in Example 1, the use of magnesium ethoxide in pyridine at reflux temperature for 96 hours gave a crude product (79% wt. yield) which, by TLC and HPLC analyses, contained an estimated yield of 16% of the title compound.

EXAMPLE 24

Under reaction conditions similar to those described in Example 1, the use of barium ethoxide (as a 10% w/v solution in ethanol) in t-amyl alcohol at 100° C. for 20 hours provided a crude product (76.5% wt. yield) which, by TLC and HPLC analyses, contained an estimated yield of 75.5% of the title compound.

EXAMPLE 25

Under reaction conditions similar to those described in Example 1, the use of titanium ethoxide in pyridine at 100° C. for 90 hours furnished a crude product (82% wt. yield) which, by TLC and HPLC analyses, container an estimated yield of 32% of the title compound.

EXAMPLE 26

Under reaction conditions similar to those described n Example 1, the use of cupric ethoxide in pyridine at 100° C. for 98 hours afforded a crude product (89.5% wt. yield) which, by TLC and HPLC analyses, contained and estimated yield of 18.5% of the title compound.

EXAMPLE 27

Under reaction conditions similar to those described in Example 1, the use of aluminium tri-t-butoxide in pyridine at 100° C. for 72 hours gave a crude product which, by TLC and HPLC analyses, contained a maximum (due to aluminium salt contamination) estimated yield of 66% of the title compound.

EXAMPLE 28

Under reaction conditions similar to those described in Example 1, the use of a total of 3.6 mol. equiv. (1.2 mol. equiv. added in three stages) of lithium diisopropylamide (as a 1.5M solution of the mono(tetrahydrofuran) complex in cyclohexane) in anhydrous 1,4-dioxan, initially at 0° C. for 15 minutes, then at room temperature for 1 hour and subsequently at 100° C. for a total of 140 hours, furnished a crude product (60.5% wt. yield) which, by TLC and HPLC analyses, contained an estimated yield of 55.5% of the title compound.

EXAMPLE 29

Under reaction conditions similar to those described in Example 1, the use of 2.0 mol.equiv. of 1,8-diazabicyclo [5.4.0]undec-7-ene in pyridine at 100° C. for 44 hours afforded a crude product (6.5% wt. yield) which, by TLC and HPLC analyses, contained an estimated yield of 3.3% of the title compound.

EXAMPLE 30

Under reaction conditions similar to those described in Example 1, the use of potassium fluoride in t-amyl alcohol at 100° C. for 44 hours gave a crude product (85% wt. yield) which, by TLC and HPLC analyses, contained an estimated yield of 3.5% of the title compound.

EXAMPLE 31

85% Potassium hydroxide pellets (3.96 g, 0.06 mol) were added to a stirred suspension of the title compound of Preparation 4 (9.85 g, 0.02 mol) in ethanol (30 ml), followed by the addition of water (30 ml) which produced a clear solution. The reaction mixture was heated under reflux for 5 hours and then the bulk of the ethanol removed by evaporation under reduced pressure. The resulting mixture was diluted with water (60 ml), its pH adjusted to 7 using dilute sulphuric acid and the precipitated product granulated for 30 minutes. The solid was collected by filtration, washed with water and dried under vacuum to provide a product (7.96 g), 96.4% of which was shown, by HPLC analysis, to be the title compound.

EXAMPLES 32–34

Under reaction conditions similar to those described in Example 1, the use of barium oxide in acetonitrile at reflux temperature for 52 hours gave the title compound (89%) of purity >99% by HPLC and TLC analyses.

Repetition using dimethylformamide as solvent at 100° C. for 31 hours provided a crude product (75.5% wt. yield) which, by TLC and HPLC analyses, contained an estimated yield of 54% of the title compound.

Further repetition using pyridine as solvent at 100° C. for 16 hours furnished a crude product which, by TLC and HPLC analyses, contained a maximum (due to barium salt contamination) estimated yield of 90% of the title compound.

EXAMPLE 35

Under reaction conditions similar to those described in Example 1, the use of cesium carbonate in 4-methylpentan-2-one (methyl isobutyl ketone) at 100° C. for 96 hours afforded a crude product (18.5% wt. yield) which, by TLC and HPLC analyses, contained an estimated yield of 13% of the title compound.

EXAMPLE 36

Under reaction conditions similar to those described in Example 1, the use of potassium bicarbonate in t-amyl alcohol at 100° C. for 115 hours gave a crude product (82.5% wt. yield) which, by TLC and HPLC analyses, contained an estimated yield of 20% of the title compound.

EXAMPLE 37

The title compound of Preparation 4 (12.32 g, 0.025 mol) was heated at 215–220° C. for 40 minutes and the resulting melt allowed to cool to room temperature. The tarry crude product was dissolved in dichloromethane (25 ml) and then purified by chromatography on silica gel, using increasingly polar mixtures of methanol in dichloromethane as eluant.

Evaporation under vacuum of the appropriate single component fractions provided the pure (by $^1$H nmr analysis) title compound (1.76 g, 14.8%), whilst a batch of less pure title compound (0.87 g, 7.3%) was obtained from further fractions. Further chromatographic processing of the latter gave an additional quantity (0.48 g) of pure title compound, the total yield being 2.24 g, 18.8%.

EXAMPLES 38–40

A stirred mixture of the title compound of Preparation 4 (12.32 g, 0.025 mol) and 1,2-dichlorobenzene (61 ml) was heated under reflux for 72 hours. The resulting dark brown reaction mixture was allowed to cool, diluted with dichloromethane (60 ml) and filtered. Evaporation under reduced pressure of the filtrate gave a solvent-containing dark brown oil (17.51 g), 28.2% of the solvent-excluded material of which was shown, by TLC and HPLC analyses, to be the title compound.

Repetition using sulpholane as solvent at about 205° C. for 5 hours provided a crude product (14% wt. yield) which, by TLC and HPLC analyses, contained an estimated yield of 12% of the title compound.

Further repetition using N-methylpyrrolidin-2-one as solvent at 205–210° C. for 3 hours provided a crude product (21.5% wt. yield) which, by TLC and HPLC analyses, contained an estimated yield of 6.5% of the title compound.

EXAMPLE 41

Under reaction conditions similar to those described in Example 38, except that the reaction was conducted for 24 hours in the presence of 4 Å molecular sieves, a solvent-containing product was obtained, 6.0% of the solvent-excluded material of which was shown, by HPLC analysis, to be the title compound.

EXAMPLE 42

Concentrated sulphuric acid (1.0 ml, 1.84 g, 18.75 mmol) was added to a stirred suspension of the title compound of Preparation 4 (12.32 g, 0.025 mol) in chlorobenzene (61 ml) and then the resulting mixture heated until solvent began to distil out. When the distillate was no longer cloudy (after collection of ca. 20 ml), the reaction mixture was allowed to cool to room temperature and a further quantity (20 ml) of chlorobenzene added before it was heated under reflux for 20 hours. The cool reaction mixture was treated with dichloromethane (100 ml) to form a solution, followed by water (100 ml). The pH of the resulting mixture was adjusted to 7 using SM aqueous sodium hydroxide solution, then the organic phase separated, combined with a dichloromethane extract (50 ml) of the aqueous phase and evaporated under reduced pressure to furnish a solid (9.51 g), 5.5% of which was shown, by HPLC analysis, to be the title compound.

EXAMPLE 43

Concentrated sulphuric acid (1.0 ml, 1.84 g, 18.75 mmol) was added to a stirred solution of the title compound of Preparation 4 (6.16 g, 12.5 mmol) in glacial acetic acid (31 ml) and the resulting mixture heated at 100° C. for 115 hours. The solvent was removed by evaporation under reduced pressure, the residue "azeotroped" with toluene (2×50 ml) and the resulting oil (10.5 g) shaken with water (60 ml) to give a crystalline solid which was collected, washed with water (10 ml) and dried. This crop (2.03 g) was combined with a second crop (3.48 g) obtained by neutralisation of the filtrate with 20% aqueous sodium hydroxide solution, followed by collection, washing and drying as before, to provide the crude product (5.51 g) which, by TLC and HPLC analyses, contained an estimated yield of 38% of the title compound.

EXAMPLE 44

A stirred mixture of the title compound of Preparation 4 (6.16 g, 12.5 mmol) and glacial acetic acid (31 ml) was heated at 100° C. for 7 hours and the resulting solution allowed to cool. TLC analysis of the reaction mixture showed that none of the title compound was present at this stage.

85% Aqueous phosphoric acid solution (0.5 ml) was added and the resulting mixture heated at 100° C., intermittently, for a total of 300 hours, then evaporated under reduced pressure. The residue was "azeotroped" with toluene and dissolved in water (50 ml), then the pH of the stirred aqueous solution adjusted to 7 with 20% aqueous sodium hydroxide solution. Stirring was continued for 2 hours, then the precipitate collected, washed with water (20 ml) and dried under vacuum at 50° C., to give the crude product (5.21 g) which, by TLC and HPLC analyses, contained an estimated yield of 9.1% of the title compound.

EXAMPLE 45

A stirred mixture of p-toluenesulphonic acid monohydrate (5.71 g, 0.030 mol) and chlorobenzene (100 ml) was heated under reflux until all the water had been removed, using a Dean-Stark trap, and then allowed to cool to room temperature. The title compound of Preparation 4 (24.64 g, 0.050 mol) was added and the reaction mixture stirred under reflux for 24 hours, then allowed to cool. To the resulting mixture was added dichloromethane (200 ml) and water (200 ml), the pH was adjusted to 7 using 2M aqueous sodium hydroxide solution, and the organic phase separated and combined with a dichloromethane extract (100 ml) of the aqueous phase. The combined organic phases were washed with water (100 ml) and evaporated under reduced pressure to afford an of,-white solid (24.86 g), 7.3% of which was shown, by TLC and HPLC analyses, to be the title compound.

EXAMPLE 46

Titanium tetrachloride (3.3 ml, 5.69 g, 0.030 mol) was added to a stirred suspension of the title compound of Preparation 4 (12.32 g, 0.025 mol) in anhydrous 1,4-dioxan (61 ml), during which vigorous evolution of a gas was noted. The stirred reaction mixture was heated at about 70° C. for 7.5 hours, allowed to cool to room temperature and then treated with water (200 ml) and concentrated hydrochloric acid (50 ml) to give a clear solution. The solution was washed with dichloromethane and its pH adjusted to 12 using 40% aqueous sodium hydroxide solution; it was then stirred for 10 minutes and its pH further adjusted to 7 using 5M hydrochloric acid. The precipitate was removed by filtration and washed with dichloromethane (2×200 ml), then the combined dichloromethane washings were used to extract the aqueous filtrate and evaporated under reduced pressure to give a solid (11.36 9), 33.7% of which was shown, by TLC and HPLC analyses, to be the title compound.

EXAMPLES 47–52

Under reaction conditions similar to those described in Example 46, the variations of which are summarised in Table 3, alternative Lewis acids provided the corrected yields of title compound shown.

TABLE 3

| EXAMPLE | LEWIS ACID | SOLVENT | REACTION TIME (HOURS) | % YIELD |
|---|---|---|---|---|
| 47 | BF$_3$* | tetrahydrofuran | 72 | 7.0 |
| 48 | AlCl$_3$ | 1,4-dioxan | 30 | 7.8 |
| 49 | FeCl$_3$ | tetrahydrofuran | 24 | 6.3 |
| 50 | ZnCl$_2$ | tetrahydrofuran | 72 | 2.8 |
| 51 | SiCl$_4$ | 1,4-dioxan | 44 | 20.5 |
| 52 | SnCl$_4$ | 1,4-dioxan | 48 | 30.8 |

*as the diethyl etherate

PREPARATION 1

5-Chlorosulohonyl-2-ethoxybenzoic acid

Molten 2-ethoxybenzoic acid (25.0 g, 0.150 mol) was added to a stirred, ice-cooled mixture of thionyl chloride (11 ml, 0.151 mol) and chlorosulphonic acid (41.3 ml, 0.621 mol), whilst maintaining the temperature of the reaction mixture below 25° C. The resulting mixture was stirred at room temperature for 18 hours and then poured into a stirred mixture of ice (270 g) and water (60 ml) to give an off-white precipitate. Stirring was continued for 1 hour, then the product was collected by filtration, washed with water and dried under vacuum to provide the title compound (36.08 g). A reference sample, m.p. 115–116° C., was obtained by crystallisation from hexane:toluene. Found: C,41.02; H,3.27. C$_9$H$_9$ClO$_5$S requires C,40.84; H,3.43%. δ (CDCl$_3$): 1.64(3H,t), 4.45(2H,q), 7.26(1H,d), 8.20(1H,dd), 8.80(1 H,d).

PREPARATION 2

2-Ethoxy-5-(4-methylpiperazin-1-ylsulphonyl)benzoic acid (a): one-step procedure 1-Methylpiperazine (33.6 ml, 0.303 mol) was added to a stirred suspension of the title compound of Preparation 1 (34.4 g, 0.130 mo.) in water (124 ml) at about 10° C., whilst maintaining the temperature of the reaction mixture below 20° C. The resulting solution was cooled to about 10° C. and, after 5 minutes, crystallisation of a solid commenced. After a further 2 hours, the solid was collected by filtration, washed with ice-water and dried under vacuum to furnish the crude product (36.7 g). A sample (15.0 g) was purified by stirring it in refluxing acetone for 1 hour; the resulting suspension was allowed to cool to room temperature and the crystalline solid collected by filtration and dried under vacuum to afford the title compound (11.7 g), m.p. 198–199° C., whose $^1$H nmr spectrum is identical with that obtained for the product of procedure (b) below.

(b): two-step procedure

A solution of the title compound of Preparation 1 (50.0 g, 0.189 mol) in acetone (150 ml) was added dropwise to a stirred mixture of 1-methylpiperazine (20.81 g, 0.208 mol) and triethylamine (28.9 ml, 0.207 mol), whilst maintaining the temperature of the reaction mixture below 20° C. A white Crystalline solid formed during the addition and stirring was continued for a further 1.5 hours. Filtration. followed by washing with acetone and drying under vacuum of the product, provided the hydrochloride-triethylamine double salt of the title compound (78.97 g), m.p. 166–169° C. Found: C,51.33; H,8.14; N,9.06; C1,8.02. C$_{14}$H$_{20}$N$_2$O$_5$S; C$_6$H$_{15}$N; HCl requires C,51.55; H,7.79; N,9.02; Cl, 7.61%. δ (CD$_3$SOCD$_3$): 1.17(9H,t), 1.32(3H,t), 2.15(3H,s), 2.47 (6H,br s), 2.86(2H,br s), 3.02(6H,q), 4.18(2H,q), 7.32(1 H,d), 7.78(1 H,dd), 7.85(1 H,d).

The double salt (30.0 g) was stirred in water (120 ml) to produce an almost clear solution, from which crystallisation of a solid rapidly occurred. After 2 hours, the solid was collected by filtration, washed with water and dried under vacuum to give the title compound (14.61 g) as a white solid. A reference sample, m.p. 201° C., was obtained by recrystallisation from aqueous ethanol. Found: C,51.09; H,6.16; N,8.43. Cl$_4$H$_{20}$N$_2$O$_5$S requires C,51.21; H,6.14; N,8.53%. δ (CD$_3$SOCD$_3$): 1.31(3H,t), 2.12(3H,s), 2.34(4H,br s), 2.84 (4H,br s), 4.20(2H,q), 7.32(1H,d), 7.80(1H,dd), 7.86(1H,d).

PREPARATION 3

4-Amino-1-methyl-3-n-propylpyrazole-5-carboxamide

A stirred suspension of 1-methyl-4-nitro-3-n-propylpyrazole-5-carboxamide (EP-A-0463756; 237.7 g, 1.12 mol) and 5% palladium on charcoal (47.5 g) in ethyl acetate (2.02 l) was hydrogenated at 344.7 kPa (50 psi) and 50° C. for 4 hours, when the uptake of hydrogen was complete. The cool reaction mixture was filtered, then the filter pad washed with ethyl acetate, the combined filtrate and washings thus furnishing an ethyl acetate solution of the title compound (EP-A-0463756) which was of sufficient purity to use directly in the next stage of the reaction sequence (see Preparation 4).

PREPARATION 4

4-[2-Ethoxy-5-(4-methylpiperazin-1-ylsulohonyl)benzamido]-1-methyl-3-n-propylpyrazole-5-carboxamide N,N'-Carbonyldiimidazole (210.8 g, 1.30 mol) was washed into a stirred suspension of the title compound of Preparation 2 (408.6 g, 1.24 mol) in ethyl acetate (1.50 l) using ethyl acetate (1.36 l) and the resulting mixture heated at 55° C. for 0.5 hour and then under reflux for a further 2 hours before being allowed to cool to room temperature. An ethyl acetate solution of the title compound of Preparation 3 (2.185 Kg of solution containing 204 g, 1.12 mol of amine) was added and the reaction mixture stirred at room temperature for 72 hours to afford a crystalline solid which was collected by filtration and dried under vacuum. The title compound (425 g), m.p. 204–206° C., thus obtained was combined with a further crop (70 g) which was recovered by concentration of the mother liquor. A reference sample, m.p. 206–208° C., was obtained by recrystallisation from aqueous methanol. Found: C,53.65; H,6.54; N,17.07. C22H$_{12}$N$_6$O$_5$S requires C,53.64; H,6.55; N,17.06%. δ (CDCl$_3$): 0.96(3H,t), 1.58(3H,t), 1.66(2H,m), 2.27(3H,s), 2.45(4H,m), 2.52(2H,t), 3.05(4H,br s), 4.05(3H,s), 4.40(2H, q), 5.61(1H, brs), 7.61(1H,d), 7.65(1H, brs), 7.90(1H,dd), 8.62(1H,d), 9.25(1H,br s).

PREPARATION 5

Methyl 2-ethoxybenzoate

Concentrated sulphuric acid (0.5 ml) was added to a solution of 2-ethoxybenzoic acid (50 9, 0.301 mol) in methanol (500 ml) and the resulting mixture heated under reflux for 70 hours, then evaporated under reduced pressure to give an oil which was dissolved in dichloromethane (300 ml). This solution was washed successively with water (150 ml), aqueous sodium bicarbonate solution (150 ml) and water (150 ml), then evaporated under reduced pressure to give the title compound (49.7 a) as an oil. δ (CDCl$_3$): 1.44 (3H,t), 3.90 (3H,s), 4.12 (2H,q), 6.95 (2H,m), 7.44 (1H,t), 7.78 (1H,d).

PREPARATION 6

Methyl 5-chlorosulphonyl-2-ethoxybenzoate

The title compound of Preparation 5 (36.04 g, 0.20 mol) was added dropwise over 10 minutes to stirred, ice-cooled chlorosulphonic acid (59.8 ml, 0.90 mol), whilst maintaining the temperature of the reaction mixture below 22° C. The reaction mixture was stirred at room temperature for 18 hours, then thionyl chloride (14.6 ml, 0.20 mol) added and the resulting solution stirred at room temperature for 6 hours, then poured into a stirred mixture of ice (530 g) and water (120 ml). The quenched mixture was extracted with dichloromethane (2×200 ml) and the combined extracts evaporated under reduced pressure to give the crude title compound (44.87 g) as a white solid. A reference sample, m.p. 99–100° C., was obtained by crystallisation from toluene. δ (CDCl$_3$): 1.52 (3H,t), 3.93 (3H,s), 4.25 (2H,q), 4.25 (2H,q), 7.12 (1H,d), 8.12 (1H,dd), 8.46 (1H,d).

PREPARATION 7

Methyl 2-ethoxy-5-(4-methylpiperazin-1-ylsulphonyl) benzoate

A solution of the crude title compound of Preparation 6 (27.87 g) in acetone (140 ml) was added dropwise over 10 minutes to a stirred, ice-cooled solution of 1-methylpiperazine (11.02 g, 0.11 mol) and triethylamine (15.3 ml, 0.11 mol) in acetone (140 ml), whilst maintaining the temperature of the reaction mixture below 20° C. A white precipitate formed during the addition and stirring was continued for a further 4 hours. The resulting mixture was filtered, the filtrate evaporated under reduced pressure and the residue azeotroped with toluene to provide a pale brown gum (41.9 g). This crude product was granulated by stirring with water (100 ml) for 2 hours and the resulting material collected by filtration, washed with water (2×50 ml) and dried under vacuum at 50° C. to furnish the title compound, m.p. 110–111° C. δ (CDCl$_3$): 1.48 (3H,t), 2.27 (3H,s), 2.47 (4H,t), 3.03 (4H,t), 3.90 (3H,s), 4.18 (2H,q), 7.04 (1H,d), 7.81 (1H,dd), 8.15 (1H,d).

The compound obtained as above was shown to be identical with that produced by conventional methyl esterification of the title compound of Preparation 2.

Furthermore, conventional base hydrolysis of the compound obtained as above afforded a product identical with that of preparation 2.

What is claimed is:

1. A compound of formula (II):

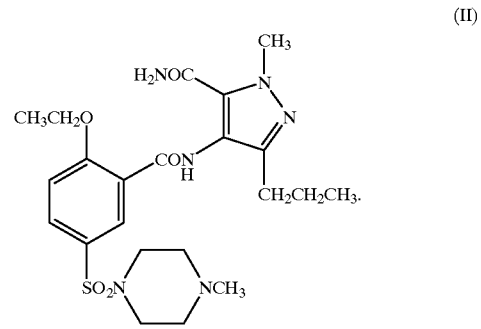

(II)

2. A compound of formula (V):

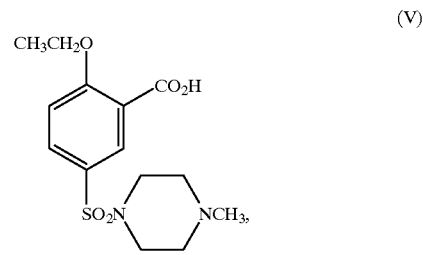

(V)

or the hydrochloride-triethylamine double salt thereof, or a $C_1$–$C_4$ alkyl ester thereof.

* * * * *